(12) United States Patent
Takahashi et al.

(10) Patent No.: US 8,648,080 B2
(45) Date of Patent: Feb. 11, 2014

(54) ACID PUMP ANTAGONIST FOR THE TREATMENT OF DISEASES INVOLVED IN ABNORMAL GASTROINTESTINAL MOTILITY

(75) Inventors: Nobuyuki Takahashi, Aichi (JP); Shinichi Koizumi, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 0 days.

(21) Appl. No.: 13/383,056

(22) PCT Filed: Jul. 9, 2010

(86) PCT No.: PCT/JP2010/061660
§ 371 (c)(1),
(2), (4) Date: Jan. 25, 2012

(87) PCT Pub. No.: WO2011/004882
PCT Pub. Date: Jan. 13, 2011

(65) Prior Publication Data
US 2012/0115820 A1    May 10, 2012

(30) Foreign Application Priority Data

Jul. 9, 2009  (JP) ................ 2009-163182
Aug. 17, 2009 (JP) ................ 2009-188464

(51) Int. Cl.
*A61K 31/497* (2006.01)
*A61K 31/44* (2006.01)

(52) U.S. Cl.
USPC ....... 514/252.13; 514/293; 514/300; 514/926

(58) Field of Classification Search
USPC .......... 514/252.13, 293, 300, 925, 926, 927
See application file for complete search history.

(56) References Cited

U.S. PATENT DOCUMENTS

| | | | |
|---|---|---|---|
| 5,750,531 A | 5/1998 | Lee et al. | |
| 6,313,137 B1 | 11/2001 | Amin et al. | |
| 6,436,953 B1 * | 8/2002 | Senn-Bilfinger | 514/293 |
| 2006/0241134 A1 | 10/2006 | Buhr et al. | |
| 2007/0142448 A1 | 6/2007 | Hanazawa et al. | |
| 2009/0048287 A1 | 2/2009 | Landau et al. | |
| 2010/0048532 A1 | 2/2010 | Koike et al. | |

FOREIGN PATENT DOCUMENTS

| | | |
|---|---|---|
| CN | 101341149 | 1/2009 |
| JP | 9-509188 | 9/1997 |
| JP | 2002-513025 | 5/2002 |
| JP | 2006-528231 | 12/2006 |
| JP | 2007-507425 | 3/2007 |
| WO | 95/18104 | 7/1995 |
| WO | 2007/072146 | 6/2007 |
| WO | 2008/035195 | 3/2008 |

OTHER PUBLICATIONS

International Search Report issued Aug. 31, 2010 in International (PCT) Application No. PCT/JP2010/061660.
Y. Matsunaga et al., "Inhibition of Phase III Activity by Acid in Canine Stomach", Regulatory Peptides, vol. 52, No. 1, pp. 61-72, 1994.
O. Yamamoto et al., "Inhibition of Motilin-Induced Phase III Contractions by Pentagastrin in Heidenhain Pouch Dogs", The Journal of Pharmacology and Experimental Therapeutics, vol. 271, No. 3, pp. 1471-1476, 1994.
K. W. Lee et al., "Dyspeptic Symptoms Associated with Hypersensitivity to Gastric Distension Induced by Duodenal Acidification", Journal of Gastroenterology and Hepatology, vol. 21, No. 3, pp. 515-520, 2006.
Motoyasu Kusano et al.; "Gastroduodenal Motor Dysfunction and Effect of H2-receptor Antagonist (H2-A) in Patients with Duodenal Ulcer (DU)"; Therapeutic Research; c. 1991; vol. 12; 23(Suppl-1); pp. 183-190 (with partial English translation).
Supplementary European Search Report issued Nov. 5, 2013 in corresponding European Application No. 10 79 7193.
H. P. Parkman et al.; "Effect of gastric acid suppressants on human gastric motility"; Gut; vol. 42, No. 2; Feb. 1998; pp. 243-250.
Y. Tomokane et al.; "Clinical Study on the Effects of Nizatidine on Gastric Motility and Cardiac Autonomic Function"; Arzneimittel-Forschung/Drug Research; vol. 54, No. 8; 2004; pp. 427-435.

* cited by examiner

*Primary Examiner* — Kevin E Weddington
(74) *Attorney, Agent, or Firm* — Wenderoth, Lind & Ponack, L.L.P.

(57) ABSTRACT

The present invention relates to a use of a compound having an acid pump antagonistic activity, a pharmaceutically acceptable salt thereof or a pharmaceutical composition thereof for the manufacture of a medicament for prevention or treatment of diseases in which abnormal gastrointestinal motility is involved. In addition, the present invention relates to the method of prevention or treatment including administering to a human or animal. The compound, the pharmaceutically acceptable salt thereof, or pharmaceutical compositions containing them, may be used in combination with one or more second active agent. Further, the present invention relates to pharmaceutical compositions and kits comprising a compound having an acid pump antagonistic activity or a pharmaceutically acceptable salt thereof for the prevention or treatment of said diseases.

7 Claims, 2 Drawing Sheets

ACID PUMP ANTAGONIST FOR THE TREATMENT OF DISEASES INVOLVED IN ABNORMAL GASTROINTESTINAL MOTILITY

This application is a U.S. national stage of International Application No. PCT/JP2010/061660 filed Jul. 9, 2010.

TECHNICAL FIELD

The present invention relates to providing a drug to normalize gastrointestinal motility. More specifically, in relation to a reversible inhibitory activity of a gastric proton pump activity, the present invention relates to a use of a compound having an acid pump antagonistic activity, a pharmaceutically acceptable salt thereof or a pharmaceutical composition thereof for the manufacture of a medicament for prevention or treatment of diseases in which abnormal gastrointestinal motility is involved. In addition, the present invention relates to the method of prevention or treatment including administering to a human or animal. The compound, the pharmaceutically acceptable salt thereof, or pharmaceutical compositions containing them, may be used in combination with one or more second active agent. Further, the present invention relates to pharmaceutical compositions and kits comprising a compound having an acid pump antagonistic activity or a pharmaceutically acceptable salt thereof for the prevention or treatment of said diseases.

BACKGROUND ART

Kusano et al have reported that a large volume of gastric acid is secreted and gastric motility decreased in the hungry condition in patients with duodenal ulcers compared with healthy human (non-patent literature 1). In addition, when gastric acid secretion is stimulated, the phase III contraction of interdigestive migrating contractions, IMC never happens in the hungry condition in dogs (non-patent literature 2 and 3). Therefore patients, who have a larger volume of gastric acid secretion than a normal volume, have been suffering from various symptoms such as abdominal distension caused by decreased gastrointestinal motility in the hungry condition, and discomfort (hereinafter may be referred to as abnormal gastrointestinal motility). Gastrointestinal tract includes stomach, duodenum, small intestine, colon (hereafter the same meaning).

CITATION LIST

Non-Patent Literatures

Non-patent Literature 1: Dig Dis Sci 38, 824-831, 1993
Non-patent Literature 2: Regul Pept 52, 61-72, 1994
Non-patent Literature 3: J Pharmacol Exp Ther 271, 1471-1476, 1994

SUMMARY OF INVENTION

Technical Problem

The unmet needs for immediate improvement of gastrointestinal motility disorders in the hungry condition is not satisfied by drugs which take several days for onset of the effect, and further gastrointestinal motility disorders in the hungry condition can not be improved because compounds forcibly stimulating the gastrointestinal motility never lead to the cooperative contraction of physiological gastrointestinal motility.

The inventors started this studies with the idea that if we find out the drugs which normalize the movement of the gastrointestinal tract in the hungry condition, these symptoms can be alleviated.

Solution to Problem

Animals (e.g., dogs) with increased gastric acid secretion may occur abnormal motility in the gastrointestinal tract in the hungry condition, and this phenomenon is thought to be a disease model reflecting a human disease condition.

Inventors of the present invention studied a group of compounds which is effective for this disease model, and reached that an acid pump antagonist improved and normalized the abnormal motility normalization. Therefore, an acid pump antagonist represented by the working examples of the present invention enhances and normalizes the gastrointestinal motility in the hungry condition, and this normalizing effect on enhancement of this gastrointestinal motility is shown to be useful in a variety of diseases caused by abnormal gastrointestinal motility, which is the first example by the present inventors.

The relationship between gastrointestinal motility and gastric acid secretion has not been apparent to those skilled in the art so far, and according to this invention, an acid pump antagonist, at least, enhance and normalize the normal gastrointestinal motility by inhibiting gastric acid secretion, which make it clear that an acid pump antagonist is effective for alleviating or preventing various symptoms of abnormal gastrointestinal motility represented by patients with duodenal ulcer.

Compounds of the present invention for preventing or treating diseases involved in gastrointestinal motility include already known compounds having an acid pump antagonistic activity and include compounds having an acid pump antagonistic activity which will be found hereafter.

Known examples of compounds having an acid pump antagonistic activity are:

the compounds disclosed in WO9955706, which are represented by AZD0865 (8-[{2,6-dimethylbenzyl}amino]-N-[2-hydroxyethyl]-2,3-dimethyl-imidazo[1,2-a]pyridin-6-carboxamide);

the compounds disclosed in WO2000017200, which are represented by soraprazan (soraprazan, (7R,8R,9R)-7-(2-methoxyethoxy)-2,3-dimethyl-9-phenyl-7,8,9,10-tetrahydroimidazo[1,2-h][1,7]naphthyridin-8-ol);

the compounds disclosed in WO9605177, which are represented by revaprazan (revaprazan, 5,6-dimethyl-2-(4-fluoro-phenylamino)-4-(1-methyl-1,2,3,4-tetrahydroisoquinoline-2-yl)pyrimidine hydrochloride);

the compounds disclosed in WO2006136552, which are represented by BYK405879 ((S)—N,N,2,3-tetramethyl-8-O-tolyl-3,6,7,8-tetrahydroisoquinoline chromeno[7,8-d]imidazole-5-carboxamide);

the compounds are disclosed in WO2000077003, which are represented by CS-526 (7-(4-fluorobenzyloxy)-2,3-dimethyl-1-{[(1S,2S)-2-methylcyclopropyl]methyl}-1H-pyrrolo[2,3-d]pyridazine);

the compounds disclosed by Takeda Pharmaceutical Co. Ltd. in WO2009041447, WO2007026916 (JPA2008-522952, JP4035559), WO2009041705, WO2008108380, and WO2007114338;

the compounds disclosed by Yuhan corporation in KR2006098908, KR2006098907, WO2006025714, WO2006025715, WO2006025717, WO2000029403, and WO2007064128;

the compounds disclosed by Nycomed GMBH-Altana Pharma AG-BYK Gulden Lomberg Chemische Fabric GMBH in WO2008095912, WO2008071765, WO2008071766, WO2008151927, WO2008084067, WO2008058990, WO2008015196, WO2007023135, WO2006117316, WO2006100254, WO2006100255, WO2006061380, WO2006037759, WO2006040338, WO2006037748, WO2006134111, WO2005121139, WO2005103057, WO2005090358, WO2005077947, WO2005070927, WO2005058325, WO2005058893, WO2005026164, WO2004087701, WO2004054984, WO2004046144, WO2003014123, WO2002030920, WO2001072756, and WO2000026217;

the compounds disclosed by Astra Zeneca AB in WO2004113338, WO2003018582, WO2000011000, WO2000010999;

the compounds disclosed by Glaxo group limited in WO2007003386 and WO2006100119;

the compounds disclosed by Ra Qualia Pharma Inc., Pfizer in WO2007072146, and WO2008035195, and so on.

Compounds described in the literature cited above, refers to all compounds described in the above cited claim 1. Also, all of the above mentioned citations are incorporated in the description herein.

Preferably, compounds following general formula (I) or (II); compounds disclosed in WO9605177 represented by revaprazan; compounds disclosed in WO2009041447, WO2007026916, WO2009041705, WO2008108380, WO2007114338, which are represented by TAK-438; compounds disclosed in WO9955706, WO2000011000, and WO2000010999, which are represented by AZD0865, or a pharmaceutically acceptable salt thereof. Compound of the present invention include solvates, complexes, polymorphs, prodrugs, isomers and isotopically-labeled compounds thereof, as described below.

A compound disclosed in WO2007072146, which is represented by the following formula (I):

A compound of the formula (I):

or a pharmaceutically acceptable salt thereof, or prodrug thereof,
wherein;
-A-B- represents —O—CH$_2$—, —S—CH$_2$—, —CH$_2$—O— or —CH$_2$—S—;
X represents an oxygen atom or NH;

$R^1$ represents a $C_1$-$C_6$ alkyl group being unsubstituted or substituted with 1 to 2 substituents independently selected from the group consisting of a hydroxy group and a $C_1$-$C_6$ alkoxy group;

$R^2$ and $R^3$ independently represent a hydrogen atom, a $C_1$-$C_6$ alkyl group, a $C_3$-$C_7$ cycloalkyl group or a heteroaryl group, said $C_1$-$C_6$ alkyl group, said $C_3$-$C_7$ cycloalkyl group and said heteroaryl group being unsubstituted or substituted with 1 to 3 substituents independently selected from the group consisting of a halogen atom, a hydroxy group, a $C_1$-$C_6$ alkoxy group, a $C_3$-$C_7$ cycloalkyl group, an amino group, a $C_1$-$C_6$ alkylamino group, and a di($C_1$-$C_6$ alkyl)amino group; or $R^2$ and $R^3$ taken together with the nitrogen atom to which they are attached form a 4 to 6 membered heterocyclic group being unsubstituted or substituted with 1 to 2 substituents selected from the group consisting of a hydroxy group, a $C_1$-$C_6$ alkyl group, a $C_1$-$C_6$ acyl group and a hydroxy-$C_1$-$C_6$ alkyl group;

$R^4$, $R^5$, $R^6$ and $R^7$ independently represent a hydrogen atom, a halogen atom, a hydroxy group, a $C_1$-$C_6$ alkyl group or a $C_1$-$C_6$ alkoxy group; and $R^8$ represents a hydrogen atom, a hydroxy group or a $C_1$-$C_6$ alkoxy group;

more preferably a compound described in the above formula (I) or a pharmaceutical acceptable salt thereof, wherein
X is an oxygen atom;
$R^2$ and $R^3$ are independently a $C_1$-$C_6$ alkyl group or a $C_3$-$C_7$ cycloalkyl group, said $C_1$-$C_6$ alkyl group and said $C_3$-$C_7$ cycloalkyl group being unsubstituted or substituted with 1 to 3 substituents independently selected from the group consisting of a halogen atom, a hydroxy group, a $C_1$-$C_6$ alkoxy group, a $C_3$-$C_7$ cycloalkyl group and a di($C_1$-$C_6$ alkyl)amino group; or $R^2$ and $R^3$ taken together with the nitrogen atom to which they are attached form an azetidinyl group, a pyrrolidinyl group, a piperazinyl group or a morpholino group, said azetidinyl group, said pyrrolidinyl group, said piperazinyl group and said morpholino group being unsubstituted or substituted with a substituent selected from the group consisting of a hydroxy group, a $C_1$-$C_6$ alkyl group, a $C_1$-$C_6$ acyl group and a hydroxy-$C_1$-$C_6$ alkyl group;

$R^4$, $R^5$, $R^6$ and $R^7$ are independently a hydrogen atom, a halogen atom or a $C_1$-$C_6$ alkyl group;
and $R^8$ is a hydrogen atom;

more preferably a compound described in the above formula (I) or a pharmaceutical acceptable salt thereof, wherein
-A-B- is —O—CH$_2$— or —CH$_2$—O—;
X is an oxygen atom;
$R^1$ is a $C_1$-$C_6$ alkyl group;
$R^2$ and $R^3$ are independently a $C_1$-$C_6$ alkyl group being unsubstituted or substituted with 1 to 3 substituents independently selected from the group consisting of a hydroxy group and a $C_1$-$C_6$ alkoxy group and; or $R^2$ and $R^3$ taken together with the nitrogen atom to which they are attached form a pyrrolidinyl group being unsubstituted or substituted with a substituent selected from the group consisting of a hydroxy group, a $C_1$-$C_6$ alkyl group and a hydroxy-$C_1$-$C_6$ alkyl group;
$R^4$, $R^5$, $R^6$ and $R^7$ are independently a hydrogen atom, a halogen atom or a $C_1$-$C_6$ alkyl group; and
$R^8$ is a hydrogen atom;

most preferably a compound described in the above formula (I) or a pharmaceutical acceptable salt thereof,
which is selected from;
4-[(5,7-difluoro-3,4-dihydro-2H-chromen-4-yl)oxy]-N,N,2-trimethyl-1H-benzimidazole-6-carboxamide;
4-[(5,7-difluoro-3,4-dihydro-2H-chromen-4-yl)oxy]-2-methyl-6-(pyrrolidin-1-ylcarbonyl)-1H-benzimidazole; and 4-[(5-fluoro-3,4-dihydro-2H-chromen-4-yl)oxy]-N,N,2-trimethyl-1H-benzimidazole-6-carboxamide.

A compound disclosed in WO2008035195, which is represented by the following formula (II).

A compound of the formula (II):

or a pharmaceutically acceptable salt thereof,
wherein;

$R^1$ represents a $C_1$-$C_6$ alkyl group being unsubstituted or substituted with 1 to 2 substituents independently selected from the group consisting of a hydroxy group, a $C_1$-$C_6$ alkoxy group, a hydroxy-substituted $C_3$-$C_7$ cycloalkyl group, a hydroxy-$C_1$-$C_6$ alkyl-substituted $C_3$-$C_7$ cycloalkyl group, an aryl group, a hydroxy-substituted aryl group, a heteroaryl group and a halogen-substituted heteroaryl group;

$R^2$ represents a hydrogen atom or a $C_1$-$C_6$ alkyl group being unsubstituted or substituted with 1 to 2 substituents independently selected from the group consisting of a hydroxy group and a $C_1$-$C_6$ alkoxy group;

$R^3$ and $R^4$ independently represent a hydrogen atom, or a $C_1$-$C_6$ alkyl, $C_3$-$C_7$ cycloalkyl or heteroaryl group being unsubstituted or substituted with 1 to 3 substituents independently selected from the group consisting of a deuterium, a halogen atom, a hydroxy group, a $C_1$-$C_6$ alkoxy group and a $C_3$-$C_7$ cycloalkyl group; or $R^3$ and $R^4$ taken together with the nitrogen atom to which they are attached form a 4 to 6 membered heterocyclic group being unsubstituted or substituted with 1 to 2 substituents selected from the group consisting of a hydroxy group, an oxo group, a $C_1$-$C_6$ alkyl group, a $C_1$-$C_6$ acyl group, and a hydroxy-$C_1$-$C_6$ alkyl group;

A represents an aryl or heteroaryl group being unsubstituted or substituted with 1 to 5 substituents independently selected from the group consisting of a halogen atom, a $C_1$-$C_6$ alkyl group, a hydroxy-$C_1$-$C_6$ alkyl group, a $C_1$-$C_6$ alkoxy-substituted $C_1$-$C_6$ alkyl group, —$NR^5SO_2R^6$ and —$CONR^7R^8$;

$R^5$, $R^7$ and $R^8$ independently represent a hydrogen atom or a $C_1$-$C_6$ alkyl group;

$R^6$ represents a $C_1$-$C_6$ alkyl group; and

E represents an oxygen atom or NH;

preferably a compound described in the above formula (II) or a pharmaceutical acceptable salt thereof, wherein $R^1$ is a $C_1$-$C_6$ alkyl group being substituted with 1 to 2 substituents independently selected from the group consisting of a hydroxy group, a $C_1$-$C_6$ alkoxy group and a heteroaryl group;

$R^2$ is a $C_1$-$C_6$ alkyl group;

$R^3$ and $R^4$ are independently a hydrogen atom or a $C_1$-$C_6$ alkyl being unsubstituted or substituted with 1 to 3 substituents independently selected from the group consisting of a deuterium, a hydroxy group and a $C_1$-$C_6$ alkoxy group; or $R^3$ and $R^4$ taken together with the nitrogen atom to which they are attached form a 4 to 6 membered heterocyclic group being unsubstituted or substituted with 1 to 2 substituent selected from the group consisting of a hydroxy group, an oxo group, a $C_1$-$C_6$ alkyl group, a $C_1$-$C_6$ acyl group and a hydroxy-$C_1$-$C_6$ alkyl group;

A is an aryl group being unsubstituted or substituted with 1 to 5 substituents independently selected from the group consisting of a halogen atom, a $C_1$-$C_6$ alkyl group, a hydroxy-$C_1$-$C_6$ alkyl group, a $C_1$-$C_6$ alkoxy-substituted $C_1$-$C_6$ alkyl group, —$NR^5SO_2R^6$ and —$CONR^7R^8$;

$R^5$, $R^7$ and $R^8$ are independently a hydrogen atom or a $C_1$-$C_6$ alkyl group; and $R^6$ is a $C_1$-$C_6$ alkyl group; and E is an oxygen atom;

more preferably a compound described in the above formula (II) or a pharmaceutical acceptable salt thereof, wherein $R^1$ is a $C_1$-$C_6$ alkyl group being substituted with a hydroxy group, a $C_1$-$C_6$ alkoxy group or a heteroaryl group;

$R^2$ is a $C_1$-$C_6$ alkyl group;

$R^3$ and $R^4$ are independently a hydrogen atom, a methyl group, —$CD_3$ or 2-hydroxyethyl group; or $R^3$ and $R^4$ taken together with the nitrogen atom to which they are attached form a morpholino group;

A is an aryl group being unsubstituted or substituted with a halogen atom; and

E is an oxygen atom;

more preferably a compound described in the above formula (II) or a pharmaceutical acceptable salt thereof, wherein $R^1$ is a $C_1$-$C_6$ alkyl group being substituted with a hydroxy group, a $C_1$-$C_6$ alkoxy group or a heteroaryl group;

$R^2$ is a $C_1$-$C_6$ alkyl group;

$R^3$ and $R^4$ are independently a hydrogen atom, a methyl group, —$CD_3$ or 2-hydroxyethyl group; or $R^3$ and $R^4$ taken together with the nitrogen atom to which they are attached form a morpholino group;

A is an aryl group being unsubstituted or substituted with a halogen atom; and

E is an oxygen atom;

most preferably a compound described in the above formula (I) or a pharmaceutical acceptable salt thereof, which is selected from;

(−)-1-(2-methoxyethyl)-N,N,2-trimethyl-8-phenyl-1,6,7,8-tetrahydrochromeno[7,8-d]imidazole-5-carboxamide;

(+8-(4-fluorophenyl)-1-(2-methoxyethyl)-N,N,2-trimethyl-1,6,7,8-tetrahydrochromeno[7,8-d]imidazole-5-carboxamide;

8-(4-fluorophenyl)-1-(3-hydroxypropyl)-N,N,2-trimethyl-1,6,7,8-tetrahydrochromeno[7,8-d]imidazole-5-carboxamide;

8-(4-fluorophenyl)-1-(isoxazol-3-ylmethyl)-N,N,2-trimethyl-1,6,7,8-tetrahydrochromeno[7,8-d]imidazole-5-carboxamide;

8-(4-fluorophenyl)-N-(2-hydroxyethyl)-1-(2-methoxyethyl)-N,2-dimethyl-1,6,7,8-tetrahydrochromeno[8,7-d]imidazole-5-carboxamide;

(8-(4-fluorophenyl)-1-(2-methoxyethyl)-2-methyl-1,6,7,8-tetrahydrochromeno[8,7-d]imidazol-5-yl)(morpholino)methanone;

or a pharmaceutically acceptable salt thereof.

A compound disclosed in WO2009041705 is represented by the following formula (I):

(I)

wherein
ring A is a saturated or unsaturated 5-membered heterocycle containing, as a ring-constituting atom besides carbon atoms, at least one heteroatom selected from a nitrogen atom, an oxygen atom and a sulfur atom;

the ring-constituting atoms $X_1$ and $X_2$ are the same or different and each is a carbon atom or a nitrogen atom, the ring-constituting atoms $X_3$ and $X_4$ are the same or different and each is a carbon atom, a nitrogen atom, an oxygen atom or a sulfur atom (provided that a pyrrole ring wherein $X_1$ is a nitrogen atom is excluded from ring A), and when the ring-constituting atoms $X_3$ and $X_4$ are the same or different and each is a carbon atom or a nitrogen atom, each ring-constituting atom optionally has substituent (s) selected from an optionally substituted alkyl group, an acyl group, an optionally substituted hydroxy group, an optionally substituted mercapto group, an optionally substituted amino group, a halogen atom, a cyano group and a nitro group;

ring B is a cyclic group containing $X_5$ and $X_6$ as ring-constituting atoms, $X_5$ is a carbon atom or a nitrogen atom, and $X_6$ is a carbon atom, a nitrogen atom, an oxygen atom or a sulfur atom;

$R^1$ is a cyclic group optionally having substituent (s);

$R^2$ is a substituent that $X_6$ optionally has when $X_6$ is a carbon atom or a nitrogen atom;

$R^3$ is an optionally substituted alkyl group, an acyl group, an optionally substituted hydroxy group, an optionally substituted mercapto group, an optionally substituted amino group, a halogen atom, a cyano group or a nitro group;

$R^4$ and $R^5$ are the same or different and each is a hydrogen atom or an alkyl group, or $R^4$ and $R^5$ optionally form, together with the adjacent nitrogen atom, an optionally substituted nitrogen-containing hererocycle;

m is 0 or 1, provided that ring B is an aryl group or a heteroaryl group, then m should be 1; and n is an integer of 0 to 3, or a salt thereof.

A compound disclosed in WO2009041447 is represented by the following formula (I):

A compound represented by the formula (I):

(I)

wherein
ring A is a saturated or unsaturated 5-membered heterocycle containing, as a ring-constituting atom besides carbon atoms, at least one heteroatom selected from a nitrogen atom, an oxygen atom and a sulfur atom, the ring-constituting atoms $X_1$ and $X_2$ are the same or different and each is a carbon atom or a nitrogen atom, the ring-constituting atoms $X_3$ and $X_4$ are the same or different and each is a carbon atom, a nitrogen atom, an oxygen atom or a sulfur atom (provided that a pyrrole ring wherein $X_1$ is a nitrogen atom is excluded from ring A), and when the ring-constituting atom $X_3$ or $X_4$ is a carbon atom or a nitrogen atom, each ring-constituting atom optionally has substituent(s) selected from an optionally substituted alkyl group, an acyl group, an optionally substituted hydroxy group, an optionally substituted mercapto group, an optionally substituted amino group, a halogen atom, a cyano group and a nitro group;

$R^1$ and $R^2$ are the same or different and each is a cyclic group optionally having substituent(s);

$R^3$ and $R^4$ are the same or different and each is a hydrogen atom or an alkyl group, or $R^3$ and $R^4$ optionally form, together with the adjacent nitrogen atom, an optionally substituted nitrogen-containing heterocycle;

Y is a spacer selected from
(1) a bond,
(2) a divalent $C_{1-6}$ hydrocarbon group optionally having substituent(s),
(3) —O—$(R^5)$m $(R^6)$n- wherein $R^5$ is a divalent $C_{1-6}$ hydrocarbon group optionally having substituent(s), $R^6$ is an oxygen atom, —S(O)w- wherein w is 0, 1 or 2, or wherein $R^7$ is a hydrogen atom, an optionally substituted hydrocarbon group, an optionally substituted $C_{1-6}$ alkyl-carbonyl or an optionally substituted $C_{1-6}$ alkylsulfonyl, m is 0 or 1, n is 0 or 1, wherein $R^8$ is a hydrogen atom, an optionally substituted hydrocarbon group, an optionally substituted $C_{1-6}$ alkyl-carbonyl or an optionally substituted $C_{1-6}$ alkylsulfonyl, $R^9$ is a divalent $C_{1-6}$ hydrocarbon group optionally having substituent(s), p is 0 or 1,

(5) —S(O)$_q$— wherein q is 0 or 1, and
(6) —S(O)r-$R^{10}$— wherein $R^{10}$ is a divalent $C_{1-6}$ hydrocarbon group optionally having substituent(s), an oxygen atom or wherein $R^{11}$ is a hydrogen atom, an optionally substituted hydrocarbon group, an optionally substituted $C_{1-6}$ alkyl-carbonyl or an optionally substituted $C_{1-6}$ alkylsulfonyl, $R^{12}$ is a divalent $C_{1-6}$ hydrocarbon group optionally having substituent(s) or —SO$_2$—, s is 0 or 1, r is 0, 1 or 2, or a salt thereof, excluding one wherein a cyclic group for $R^2$ has an aminosulfonyl group as a substituent, N-methyl-1-[1-phenyl-2-(phenylthio)-1H-imidazol-4-yl]methanamine and 1-[4-phenyl-5-(phenylthio)-1,3-thiazol-2-yl]methanamine.

A compound disclosed in WO2008108380 is represented by the following formula (I):

(I)

wherein $R^1$ is an optionally substituted cyclic group,
$R^2$ is a substituent,
$R^3$ is an optionally substituted alkyl group, an acyl group, an optionally substituted hydroxy group, an optionally substituted amino group, a halogen atom, a cyano group or a nitro group,
$R^4$ and $R^5$ are the same or different and each is a hydrogen atom, an optionally substituted alkyl group, an acyl group, an optionally substituted hydroxy group, an optionally substituted amino group, a halogen atom, a cyano group or a nitro group,
$R^6$ and $R^{6'}$ are the same or different and each is a hydrogen atom or an alkyl group, and
n is an integer of 0 to 3, provided that 1-[5-(2-fluoropyridin-3-yl)-1-(pyridin-3-ylsulfonyl)-1H-pyrrol-3-yl]-N-methylmethanamine, 1-[5-(2-chloropyridin-3-yl)-1-(pyridin-3-ylsulfonyl)-1H-pyrrol-3-yl]-N-methylmethanamine, 1-{5-(2-fluoropyridin-3-yl)-1-[(6-methoxypyridin-3-yl)sulfonyl]-1H-pyrrol-3-yl}-N-methylmethanamine, N-methyl-1-[5-(2-methylpyridin-3-yl)-1-(pyridin-3-ylsulfonyl)-1H-pyrrol-3-yl]methanamine, 1-{5-(2-fluoropyridin-3-yl)-1-[(6-methylpyridin-3-yl)sulfonyl]-1H-pyrrol-3-yl}-N-methylmethanamine, and 1-[4-chloro-5-(2-fluoropyridin-3-yl)-1-(pyridin-3-ylsulfonyl)-1H-pyrrol-3-yl]-N-methylmethanamine are excluded, or a salt thereof.

A compound disclosed in WO2007114338 is represented by the formula (I):
An acid secretion inhibitor comprising a compound represented by the formula (I)

(I)

wherein ring A is a saturated or unsaturated 5- or 6-membered ring group optionally having, as a ring-constituting atom besides carbon atom, 1 to 4 hetero atoms selected from a nitrogen atom, an oxygen atom and a sulfur atom, ring-constituting atoms $X^1$ and $X^2$ are each a carbon atom or a nitrogen atom, a ring-constituting atom $X^3$ is a carbon atom, a nitrogen atom, an oxygen atom or a sulfur atom, $R^1$ is an optionally substituted aryl group or an optionally substituted heteroaryl group, $R^2$ is an optionally substituted alkyl group, an optionally substituted aryl group or an optionally substituted heteroaryl group, $R^3$ is an aminomethyl group optionally substituted by 1 or 2 lower alkyl groups, which is a substituent on a ring-constituting atom other than $X^1$, $X^2$ and $X^3$, ring A optionally further has substituent(s) selected from a lower alkyl group, a halogen atom, a cyano group and an oxo group, excluding a compound represented the formula wherein each symbol is as defined above, a pyrrole ring optionally further has substituent(s) selected from a lower alkyl group, a halogen atom, a cyano group and an oxo group or a salt thereof, or a prodrug thereof.

A compound disclosed in WO2008-522952 (P2008-522952A, WO200726916), which is represented by the following formula (I):

(I)

wherein $R^1$ is a monocyclic nitrogen-containing heterocyclic group optionally condensed with a benzene ring or a heterocycle, the monocyclic nitrogen-containing heterocyclic group optionally condensed with a benzene ring or a heterocycle optionally has substituent (s), $R^2$ is an optionally substituted $C_{6-14}$ aryl group, an optionally substituted thienyl group or an optionally substituted pyridyl group, $R^3$ and $R^4$ are each a hydrogen atom, or one of $R^3$ and $R^4$ is a hydrogen atom and the other is an optionally substituted lower alkyl group, an acyl group, a halogen atom, a cyano group or a nitro group, and $R^5$ is an alkyl group or a salt thereof.

A compound described in JP4035559, WO2007026916 is as follows:
(1) 1-{5-(2-Fluorophenyl)-1-[(6-methylpyridin-3-yl)sulfonyl]-1H-pyrrol-3-yl}-N-methylmethanamine or a salt thereof.
(2) 1-[4-Fluoro-5-phenyl-1-(pyridin-3-ylsulfonyl)-1H-pyrrol-3-yl]-N-methylmethanamine or a salt thereof.
(3) N-Methyl-1-[5-(4-methyl-3-thienyl)-1-(pyridin-3-ylsulfonyl)-1H-pyrrol-3-yl]methanamine or a salt thereof.
(4) 1-[5-(2-Fluorophenyl)-1-(pyridin-3-ylsulfonyl)-1H-pyrrol-3-yl]-N-methylmethanamine or a salt thereof.
(5) N-Methyl-1-[5-(2-methylphenyl)-1-(pyridin-3-ylsulfonyl)-1H-pyrrol-3-yl]methanamine or a salt thereof.

DESCRIPTION OF EMBODIMENT

Example 1

Beagle dogs surgically wearing a force transducer at gastric antrum and serosal side of duodenum were used, and the motion of the gastric antrum and duodenum under wakefulness were observed. After confirming the phase III in the hungry condition, gastric acid secretion was stimulated by pentagastrin subcutaneous infusion (6 microg/kg/hr). Pentagastrin infusion was continued until the end of the study. After about 2 hours from pentagastrin infusion, an acid pump antagonist (compound A) was orally administered, and then gastrointestinal motility was continuously observed for 2-3 hours.

Figure 1:
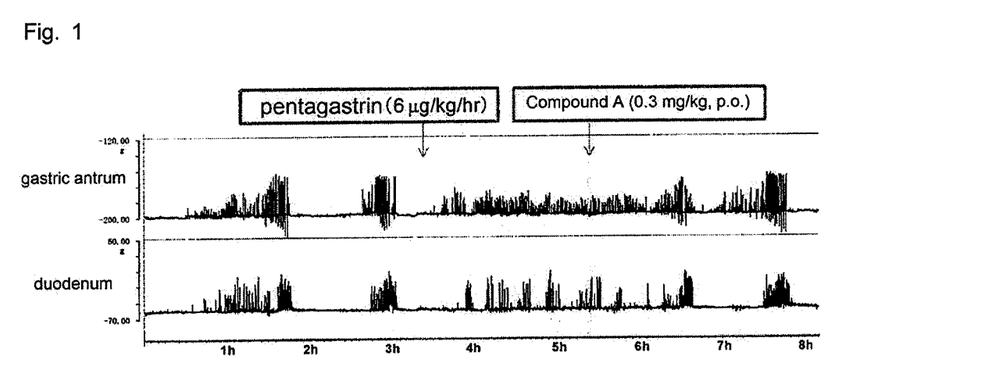
FIG. 1 shows the effect on an acid pump antagonist (compound A) against gastrointestinal motility in the gastric antrum and duodenum.

The results are shown in FIG. 1. In FIG. 1, the horizontal axis represents the time at measuring, and the vertical axis represents the gastrointestinal contraction towards muscle bridge of gastric antrum or duodenum.

The phase III contraction disappeared by pentagastrin stimulation, 6 microg/kg/hr, which is known to promote gastric acid secretion; and uncoordinated contraction, which is different from the contraction of postprandial period with solid food, occurred in the stomach and duodenum. After about 2 hours from pentagastrin stimulation, when compound A ((−)-1-(2-methoxyethyl)-N,N,2-trimethyl-8-phenyl-1,6,7,8-tetrahydrochromeno[7,8-d]imidazole-5-carboxamide (Acid Pump Antagonist, APA) was orally administered at the dose of 0.3 mg/kg, the contraction of the duodenum was initially tended to subside, and then at one hour after administration, the phase III contraction occurred in the stomach and duodenum. After that, the normal IMC occurred.

Example 2

Figure 2:
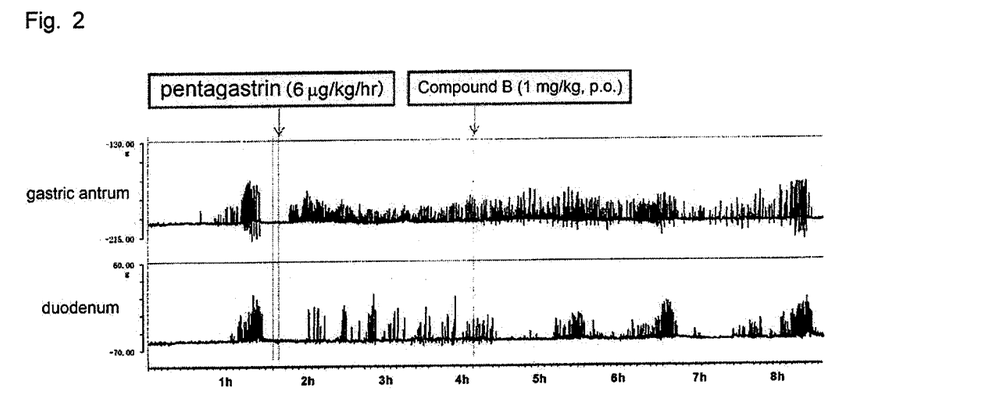
FIG. 2 shows the effect on an acid pump antagonist (compound B) against gastrointestinal motility in the gastric antrum and duodenum.

By the similar method to Example 1, an acid pump antagonist, compound B ((S)-(−)-4-[(5,7-difluoro-3,4-dihydro-2H-chromen-4-yl)oxy]-N,N,2-trimethyl-1H-benzimidazole-6-carboxamide) was orally administered 1 mg/kg. The results are shown in FIG. 2. In FIG. 2, the horizontal axis represents the time at measuring, and the vertical axis represents the gastrointestinal contraction towards muscle bridge of gastric antrum or duodenum. As similar to Example 1, the contraction of the duodenum was initially subsided, and then soon (within one hour after dosing) IMC occurred. After the phase III contraction, the contraction motion moved to a resting state (phase I).

Example 3

Figure 3:
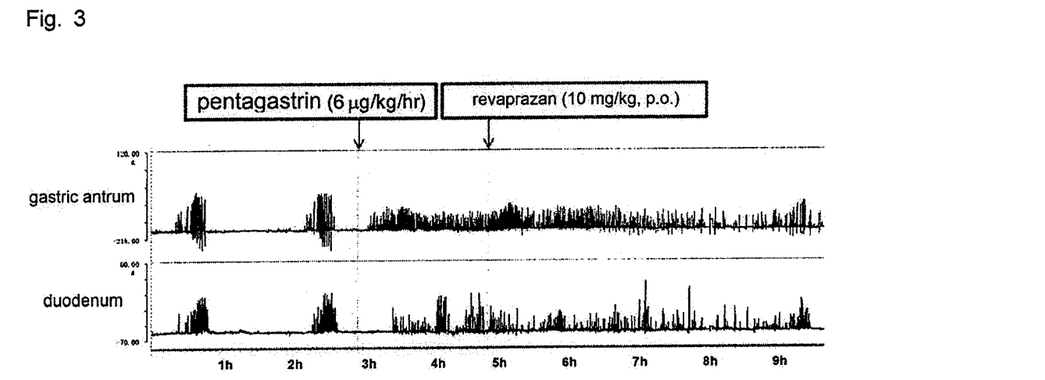
FIG. 3 shows the effect on an acid pump antagonist (revaprazan) against gastrointestinal motility in the gastric antrum and duodenum.

By the similar method to Example 1, the results of oral administration of acid pump antagonist, revaprazan 10 mg/kg are shown in FIG. 3. As similar to Example 1, the contraction of the duodenum was initially subsided, and soon (within one hour after dosing) the irregular contraction was tended gradually to subside, and then IMC occurred; After the phase III contraction, the contraction motion moved to a resting state (phase I).

Example 4

Figure 4:
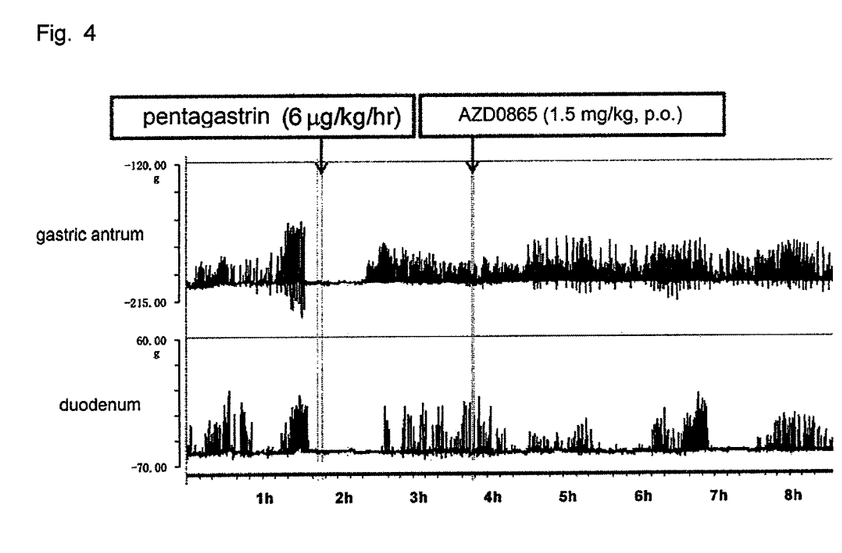
FIG. 4 shows the effect on an acid pump antagonist (AZD0865) against gastrointestinal motility in the gastric antrum and duodenum.

By the similar method to Example 1, the results of oral administration of acid pump antagonist, AZD0865 1.5 mg/kg are shown in FIG. 4. As similar to Example 1, the contraction of the duodenum was initially subsided, and soon (within one hour after dosing) the irregular contraction was tended gradually to subside, and then IMC occurred. After the phase III contraction, the contraction motion moved to a resting state (phase I).

It has been established that proton pump inhibitors (PPI) are prodrugs that undergo an acid-catalyzed chemical rearrangement that permits them to inhibit $H^+/K^+$-ATPase by covalently biding to its Cystein residues (Sachs, G. et. al., Digestive Diseases and Sciences, 1995, 40, 3S-23S; Sachs et. al., Annu Rev Pharmacol Toxicol, 1995, 35, 277-305.). However, unlike PPIs, acid pump antagonists inhibit acid secretion via reversible potassium-competitive inhibition of $H^+/K^+$-ATPase. SCH28080 is one of such reversible inhibitors and has been studied extensively. Other newer agents (revaprazan, soraprazan, AZD-0865 and CS-526) have entered in clinical trials confirming their efficacy in human (Pope, A.; Parsons, M., Trends in Pharmacological Sciences, 1993, 14, 323-5; Vakil, N., Alimentary Pharmacology and Therapeutics, 2004, 19, 1041-1049). In general, acid pump antagonists are found to be useful for the treatment of a variety of diseases, including gastrointestinal disease, gastroesophageal disease, gastroesophageal reflux disease (GERD), peptic ulcer, gastric ulcer, duodenal ulcer, non-steroidal anti-inflammatory drug (NSAID)-induced ulcers, gastritis, infection of *Helicobacter pylori*, dyspepsia, functional dyspepsia, Zollinger-Ellison syndrome, non-erosive reflux disease (NERD), visceral pain, heartburn, nausea, esophagitis, dysphagia, hypersalivation, airway disorders or asthma (Kiljander, Toni O, American Journal of Medicine, 2003, 115 (Suppl. 3A), 65S-71S.).

As described above, an acid pump antagonist is known to suppress gastric acid secretion and has been shown to be useful for a variety of diseases caused by this effect. However, under the current status of research in this area, the fact that the acid pump antagonist enhances gastrointestinal motility has never been found so far and in addition, the relationship between gastric acid secretion and gastrointestinal motility is not apparent. Therefore, the fact that suppressing gastric acid secretion enhances the gastrointestinal motility can not be foreseen for those skilled in the art, which is the base of this invention that an acid pump antagonist is useful as a gastrointestinal function adjustment drug and a gastrointestinal motility activation drug for the treatment of diseases caused by abnormal gastrointestinal motility. For example, the digestive system (e.g. stomach or intestine) loses their motor function to cause constipation, and long-term constipation condition induces colon cancer, bowel obstruction, and bowel infarction because decomposed materials of food retain in the intestine for long periods. The present invention is useful for preventing or treating such diseases.

CCK-A antagonists, β3 agonist, neurotensin antagonists, opioid agonists, NK1 antagonists, NK2 antagonists, 5-HT1A agonists, muscarinic agonists, 5-lipoxygenase inhibitors, CRF antagonists, etc. have been conventionally known as a gastrointestinal function adjustment drug and a gastrointestinal motility activation drug, but however an acid pump antagonist has never been known to be useful for a gastrointestinal function adjustment drug and a gastrointestinal motility activation drug. The present invention shows that an acid pump antagonist is effective as a gastrointestinal function adjustment drug and a gastrointestinal motility activation drug, which makes a high industrial contribution as new drug therapies.

A compound of the invention exhibits acid pump inhibitory activity. An acid pump antagonist of the present invention may be usefully combined with another pharmacologically active compound, or with two or more other pharmacologically active compounds.

As discussed above, a compound of the invention exhibits acid pump inhibitory activity. An acid pump antagonist of the present invention may be usefully combined with another pharmacologically active compound; or with two or more other pharmacologically active compounds. For example, an acid pump antagonist, particularly a compound of the formula (I), or a pharmaceutically acceptable salt thereof, as defined above, may be administered simultaneously, sequentially or separately in combination with one or more agents selected from:

(i) histamine $H_2$ receptor antagonists, e.g. ranitidine, lafutidine, nizatidine, cimetidine, famotidine and roxatidine;
(ii) proton pump inhibitors, e.g. omeprazole, esomeprazole, pantoprazole, rabeprazole, tenatoprazole, ilaprazole and lansoprazole;
(iii) oral antacid mixtures, e.g. Maalox®, Aludrox® and Gaviscon®;
(iv) mucosal protective agents, e.g. polaprezinc, ecabet sodium, rebamipide, teprenone, cetraxate, sucralfate, chloropylline-copper and plaunotol;
(v) anti-gastric agents, e.g. Anti-gastrin vaccine, itriglumide and Z-360;
(vi) 5-$HT_3$ antagonists, e.g. dolasetron, palonosetron, alosetron, azasetron, ramosetron, mitrazapine, granisetron, tropisetron, E-3620, ondansetron and indisetron;
(vii) 5-$HT_4$ agonists, e.g. tegaserod, mosapride, cinitapride and oxtriptane;
(viii) laxatives, e.g. Trifyba®, Fybogel®, Konsyl®, Isogel®, Regulan®, Celevac® and Normacol®;
(ix) GABAB agonists, e.g. baclofen and AZD-3355;
(x) $GABA_B$ antagonists, e.g. GAS-360 and SGS-742;
(xi) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;
(xii) dopamine antagonists, e.g. metoclopramide, domperidone and levosulpiride;
(xiii) Tachykinin (NK) antagonists, particularly NK-3, NK-2 and NK-1 antagonists, e.g. nepadutant, saredutant, talnetant, (αR,9R)-7-[3,5-bis(trifluoromethyl)benzyl]-8,9,10,11-tetrahydro-9-methyl-5-(4-methy!phenyl)-7H-[1,4]diazocino[2,1-g][1,7]naphthridine-6-13-dione (TAK-637), 5-[[(2R,3S)-2-[1R)-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S);
(xiv) *Helicobacter pylori* infection agents, e.g. clarithromicyn, roxitamycin, rokitamycin, flurithromycin, telithromycin, amoxicillin, ampicillin, temocillin, bacampicillin, aspoxicillin, sultamicillin, piperacillin, ienampicillin, tetracycline, metronidazole, bithmuth citrate and bithmuth subsalicylate;
(xv) nitric oxide synthase inhibitors, e.g. GW-274150, tilarginine, P54, guanidioethyldisulfide and nitroflurbiprofen;
(xvi) vanilloid receptor 1 antagonists, e.g. AMG-517 and GW-705498;
(xvii) muscarinic receptor antagonists, e.g. trospium, solifenacin, tolterodine, tiotropium, cimetropium, oxitropium, ipratropium, tiquizium, dalifenacin and imidafenacin;
(xviii) calmodulin antagonists, e.g. squalamine and DY-9760;
(xix) potassium channel agonists, e.g. pinacidil, tilisolol, nicorandil, NS-8 and retigabine;
(xx) beta-1 agonists, e.g. dobutamine, denopamine, xamoterol, denopamine, docarpamine and xamoterol;
(xxi) beta-2 agonists, e.g. salbutamol; terbutaline, arformoterol, meluadrine, mabuterol, ritodrine, fenoterol, clenbuterol, formoterol, procaterol, tulobuterol, pirbuterol, bambuterol, tulobuterol, dopexamine and levosalbutamol;
(xxii) beta agonists, e.g. isoproterenol and terbutaline;
(xxiii) alpha 2 agonists, e.g. clonidine, medetomidine, lofexidine, moxonidine, tizanidine, guanfacine, guanabenz, talipexole and dexmedetomidine;
(xxiv) endthelin A antagonists, e.g. bonsetan, atrasentan, ambrisentan, clazosentan, sitaxsentan, fandosentan and darusentan;
(xxv) opioid p agonists, e.g. morphine, fentanyl and loperamide;
(xxvi) opioid p antagonists, e.g. naloxone, buprenorphine and alvimopan;
(xxvii) motilin agonists, e.g. erythromycin, mitemcinal, SLV-305 and atilmotin;
(xxviii) ghrelin agonists, e.g. capromorelin and TZP-101;
(xxix) AchE release stimulants, e.g. Z-338 and KW-5092;
(xxx) CCK-B antagonists, e.g. itriglumide, YF-476 and S-0509;
(xxxi) glucagon antagonists, e.g. N,N-2501 and A-770077;
(xxxii) piperacillin, lenampicillin, tetracycline, metronidazole, bithmuth citrate and bithmuth subsalicylate;
(xxxiii) Glucagon-like peptide-1 (GLP-1) antagonists, e.g. PNU-126814;
(xxxiv) small conductance calcium-activated potassium channel 3 (SK-3) antagonists, e.g. apamin, dequalinium, atracurium, pancuronium and tubocurarine;
(xxxv) mGluR5 anatagonists, e.g. ADX-10059 and AFQ-056;
(xxxvi) 5-HT3 agonists, e.g. pumosetrag (DDP733);
(xxxvii) mGluR8 agonists, e.g. (S)-3,4-DCPG and mGluR8-A.

In terms of pharmaceutically acceptable acid addition salts, suitable acid addition salts are formed from acids which form non-toxic salts. Examples include acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically, acceptable salt of a compound having an acid pump antagonistic activity may be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

Pharmaceutically acceptable salts of the compounds of the present invention include both unsolvated and solvated forms. The term "solvate" is used herein to describe a molecular complex comprising a compound of the invention and one or more pharmaceutically acceptable solvent molecules, for example, ethanol.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sd. 64 (8), 1269-1288 by Haleblian (August 1975).

All references to a compound having an acid pump antagonistic activity include references to salts and complexes thereof and to solvates and complexes of salts thereof.

A compound having an acid pump antagonistic activity includes polymorphs, prodrugs, and isomers thereof (including optical, geometric and tautomeric isomers) and isotopically-labeled compounds of the present invention as herein defined.

As mentioned above, this invention includes all polymorphs as herein before defined.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "prodrugs". Further information on the use of prod rugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H Bundgaard (Elsevier, 1985).

Some examples of prodrugs in accordance with the invention include:
(i) where the compound of this invention contains a carboxylic acid functionality (—COON), an ester thereof, for example, replacement of the hydrogen of —COOH with ($C_1$-$C_6$)alkanoyloxymethyl;
(i) where the compound of this invention contains an alcohol functionality (—OH), an ether thereof, for example, replacement of the hydrogen of —OH with ($C_1$-$C_6$)alkanoyloxymethyl; and
(iii) where the compound of formula (I) contains a primary or secondary amino functionality (—$NH_2$ or —NHR where R is not H), an amide thereof, for example, replacement of one or both hydrogens of —$NH_2$ or NHR with ($C_1$-$C_{10}$)alkanoyl.

Further examples of replacement groups in accordance with the foregoing examples are well known in the art and examples of other prodrug types may be found in the aforementioned references, but are not limited to these.

Certain compounds having an acid pump antagonistic activity may themselves act as prodrugs of other compounds of this invention.

Compounds of this invention containing one or more asymmetric carbon atoms can exist as two or more stereoisomers. Where a compound of this invention contains an alkenyl or alkenylene group, geometric cis/trans (or ZIE) isomers are possible. Where the compound contains, for example, a keto or oxime group, an aromatic moiety or a heteroaromatic ring including nitrogen of more than two, tautomeric isomerism ('tautomerism') can occur. It follows that a single compound may exhibit more than one type of isomerism.

Included within the scope of the present invention are all stereoisomers, geometric isomers and tautomeric forms of the compounds of this invention, including compounds exhibiting more than one type of isomerism, and mixtures of one or more thereof. Also included are acid addition or base salts wherein the counter ion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to those skilled in the art.

Chiral compounds of having acid pump antagonistic activity (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of this invention wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection.

Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds having an acid pump antagonistic activity can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Therefore the present invention provides the combination comprising a compound having an acid pump antagonistic activity, its solvate or prodrug, and a compound (or a compound group as a second active agent) selected from one or more pharmaceutically active drugs. In addition, the present invention provides a pharmaceutical composition comprising such combination together with a pharmaceutically acceptable additive, diluent or carrier, especially for the treatment of a variety of diseases caused by abnormal gastrointestinal motility. Further, the present invention provides a kit comprising a first pharmaceutical composition containing a compound having an acid pump antagonistic activity or a pharmaceutically acceptable salt thereof; a second active agent; and a container.

A kit comprising a compound having an acid pump antagonistic activity, or a pharmaceutically acceptable salt thereof for the treatment of a variety of diseases caused by abnormal gastrointestinal motility is one of the present inventions. A commercial package comprising the pharmaceutical composition containing the compound having an acid pump antagonistic activity, or a pharmaceutically acceptable salt thereof and a written matter associated therewith, wherein the written matter states that the compound can or should be used for treating a variety of diseases caused by abnormal gastrointestinal motility.

The term "treating", as used herein, refers to reversing, alleviating, inhibiting the progress of, or preventing the disorder or condition to which such term applies, or one or more symptoms of such disorder or condition. The term "treatment" as used herein includes not only treating diseases caused by abnormal gastrointestinal motility but also broadly includes relieving symptoms, improving QOL and the concept of so-called prevention.

Other features and advantages of the invention will be apparent from the following detailed description and from the claims. While the invention is described in connection with specific embodiments, other changes and modifications that may be practiced are also part of this invention and are also within the scope of the appendant claims, including departures from the present disclosure that come within known or customary practice within the art. This application is intended to cover any equivalents, variations, uses, or adaptations of the invention that follow, in general, the principles of the invention.

A compound having an acid pump antagonistic activity are administered in a dose sufficient to enhance a variety of diseases caused by abnormal gastrointestinal motility. Such therapeutically effective amounts will be determined using routine optimization techniques that are dependent on the particular condition to be treated, the condition of the patient, the route of administration, the formulation, the judgment of the practitioner, and other factors evident to those skilled in the art in light of this disclosure.

A compound having an acid pump antagonistic activity can be incorporated into a therapeutic composition. Such a pharmaceutical agent are combined with a pharmaceutically acceptable delivery vehicle or carrier.

A pharmaceutically acceptable delivery vehicle includes solvents, dispersion media, coatings, antibacterial and antifungal agents, and isotonic and absorption delaying agents that are compatible with pharmaceutical administration. The vehicle may also include other active or inert components.

Therapeutic efficacy of a compound having an acid pump antagonistic activity can be determined in light of this disclosure by standard therapeutic procedures in cell cultures or experimental animals, e.g., for determining the ED50 (the dose therapeutically effective in 50% of the population).

The data obtained from the cell culture assays and animal studies can be used in formulating a range of dosage for use in humans. The dosage may vary depending upon the formulation and the route of administration. For any acid pump antagonists used in the method of the invention, the therapeutically effective dose can be estimated initially from cell culture assays. A dose may be formulated in animal models to achieve a circulating plasma concentration range that includes the IC$_{50}$ as determined in cell culture. Such information can be used to more accurately determine useful doses in humans. Levels in plasma may be measured, for example, by high performance liquid chromatography and mass spectrometer.

The skilled artisan will appreciate that certain factors may influence the dosage and timing required to effectively treat a mammal including, but not limited to, the severity of the disease or disorder, previous treatments, the general health and/or age of the mammal, and other diseases present. Moreover, treatment of a mammal with a therapeutically effective amount of a compound having an acid pump antagonistic activity can include a single treatment, an intermittent treatment, or a series of treatments, but not limited to these.

Particularly the precise amount of the compounds administered to a human patient will be the responsibility of the attendant physician. However, the dose employed will depend upon a number of factors including the age and sex of the patient, the precise condition being treated and its severity, and the route of administration.

The compounds having an acid pump antagonistic activity are conveniently administered in the form of pharmaceutical compositions. Such compositions may conveniently be presented for use in conventional manner in admixture with one or more physiologically acceptable carriers or excipients. Compositions comprising a compound having an acid pump antagonistic activity can be also one of the inventions.

While it is possible for the compounds having an acid pump antagonistic activity to be administered as the raw chemical, it is preferable to present it as a pharmaceutical formulation. The formulations comprise the compounds together with one or more acceptable carriers or diluents therefor and optionally other therapeutic ingredients. The carrier(s) must be acceptable in the sense of being compatible with the other ingredients of the formulation and not deleterious to the recipient thereof.

A therapeutic composition is formulated to be compatible with its intended route of administration. Non-limiting examples of routes of administration include parenteral, e.g., intravenous, intradermal, subcutaneous, oral (e.g., by ingestion or inhalation), transdermal (topical), transmucosal, and rectal administration. Solutions or suspensions can be made as described in Remington's Pharmaceutical Sciences, (18I 1 ed., Gennaro, ed., Mack Publishing Co., Easton, Pa., (1990)).

The most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds having an acid pump antagonistic activity or pharmaceutically acceptable salts thereof may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

The present invention also relates to combining separate pharmaceutical compositions in kit form. The kit comprises two separate pharmaceutical compositions: a compound of the present invention, a prodrug thereof or a pharmaceutically acceptable salt of said compound or said prodrug; and a second therapeutic agent as described herein. The kit comprises a container for containing the separate compositions such as a divided bottle or a divided foil packet, however, the separate compositions may also be contained within a single, undivided container. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

Exemplary Methods of Combination Therapy

In certain embodiments; the methods provided herein comprise administering a compound having an acid pump antagonistic activity in combination with one or more second active agents, and/or in combination with radiation therapy or surgery. The administration of a compound having an acid pump antagonistic activity and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., Physicians' Desk References.

In one embodiment, a compound having an acid pump antagonistic activity or the second active agent is administered intravenously or subcutaneously and once or twice daily in an amount of from about 0.1 to about 3,000 mg, preferably from about 1 to about 1,000 mg, more preferably from about 5 to about 500 mg or most preferably from about 10 to about 375 mg or most preferably from about 50 to about 200 mg.

In another embodiment, provided herein are methods of treating, preventing and/or managing a variety of diseases caused by abnormal gastrointestinal motility, which comprise administering a compound having an acid pump antagonistic activity in conjunction with (e.g., before, during or after) conventional therapy including, but not limited to, other non-drug based therapy presently used. Without being limited by theory, it is believed that a compound having an acid pump antagonistic activity may provide additive or synergistic effects when given concurrently with conventional therapy.

In certain embodiments, the second active agent is co-administered with a compound having an acid pump antagonistic activity or administered with 1-50 hours delay. In certain embodiments, a compound having an acid pump antagonistic activity is administered first followed by administration with the second active agent with 1-50 hours delay. In other embodiments, the second active agent is administered first followed by administration of a compound having an acid pump antagonistic activity with 1-50 hours delay. In some embodiment, the delay is 24 hours.

In one embodiment, a compound having an acid pump antagonistic activity can be administered in an amount of from about 0.1 to about 3,000 mg/day alone or in combination with a second active agent disclosed herein, prior to, during, or after the use of conventional therapy.

In another embodiment, the methods provided herein comprise: a) administering to a patient in need thereof, a dose of about 0.1 to about 3,000 mg/day of a compound having an acid pump antagonistic activity and b) administering a therapeutically effective amount of a second active agent such as a supportive care agent.

The administration mode of the compound having an acid pump antagonistic activity and the concomitant drug is not particularly limited, and the compound of the present invention and the concomitant drug only need to be combined on administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like. In the following, these administration modes are collectively abbreviated as the concomitant drug of the present invention.

When the compounds having an acid pump antagonistic activity are used in combination with one or more other therapeutic agents (second active agents), the compounds may be administered either sequentially or simultaneously by any convenient route.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound having an acid pump antagonistic activity is used in combination with a second therapeutic agent active against the same disease, the dose of each compound may differ from that when the compound is used alone. Appropriate doses will be readily appreciated by those skilled in the art.

Likewise, when a compound having an acid pump antagonistic activity is used in combination with a second therapeutic agent active against the same disease, the dose of each compound may differ from that when the compound is used alone. Appropriate doses will be readily appreciated by those skilled in the art.

Preferred unit dosage formulations are those containing an effective daily dose, as herein above recited, or an appropriate fraction thereof, of the active ingredient. For example, a daily dose of a compound having an acid pump antagonistic activity may be from 0.1 mg to 3,000 mg, more preferably about 1 mg to 1,000 mg. As mentioned above, a dose may depend on the condition of individual patients, and is not limited to these.

Suitable subject to be administered a compound having an acid pump antagonist activity or a pharmaceutical composition containing the compound is a mammal, including humans. Among them, a mammal with a variety of diseases caused by abnormal gastrointestinal motility is preferable. A mammal with low gastric pH caused by gastric acid secretion is more preferable.

The invention claimed is:

1. A method for adjusting a gastrointestinal function or activating a gastrointestinal motility in a disease in which abnormal gastrointestinal motility is involved, in a human or an animal, which comprises administering to the human or the animal in need a therapeutically effective amount of a compound having an acid pump antagonistic activity or a pharmaceutically acceptable salt thereof.

2. The method according to claim 1, wherein the compound or salt having the acid pump antagonistic activity is selected from the group consisting of:
(1) (S)-(+4-[(5,7-difluoro-3,4-dihydro-2H-chromen-4-yl) oxy]-N,N,2-trimethyl-1H-benzimidazole-6-carboxamide;
(2) (S)-(+4-[(5,7-difluoro-3,4-dihydro-2H-chromen-4-yl) oxy]-2-methyl-6-(pyrrolidin-1-ylcarbonyl)-1H-benzimidazole;
(3) (S)-(−)-4-[(5-fluoro-3,4-dihydro-2H-chromen-4-yl) oxy]-N,N,2-trimethyl-1H-benzimidazole-6-carboxamide;
(4) (−)-1-(2-methoxyethyl)-N,N,2-trimethyl-8-phenyl-1, 6,7,8-tetrahydrochromeno[7,8-d]imidazole-5-carboxamide;
(5) (+8-(4-fluorophenyl)-1-(2-methoxyethyl)-N,N,2-trimethyl-1,6,7,8-tetrahydrochromeno[7,8-d]imidazole-5-carboxamide;
(6) 8-(4-fluorophenyl)-1-(3-hydroxypropyl)-N,N,2-trimethyl-1,6,7,8-tetrahydrochromeno[7,8-d]imidazole-5-carboxamide;
(7) 8-(4-fluorophenyl)-1-(isoxazol-3-ylmethyl)-N,N,2-trimethyl-1,6,7,8-tetrahydrochromeno[7,8-d]imidazole-5-carboxamide;
(8) 8-(4-fluorophenyl)-N-(2-hydroxyethyl)-1-(2-methoxyethyl)-N,2-dimethyl-1,6,7,8-tetrahydrochromeno[8,7-d]imidazole-5-carboxamide;
(9) (8-(4-fluorophenyl)-1-(2-methoxyethyl)-2-methyl-1, 6,7,8-tetrahydrochromeno[8,7-d]imidazol-5-yl)(morpholino)methanone;
(10) 1-{5-(2-fluorophenyl)-1-[(6-methylpyridin-3-yl)sulfonyl]-1H-pyrrol-3-yl}-N-methylmethanamine;
(11) 1-[4-fluoro-5-phenyl-1-(pyridin-3-ylsulfonyl)-1H-pyrrol-3-yl]-N-methylmethanamine;
(12) N-methyl-1-[5-(4-methyl-3-thienyl)-1-(pyridin-3-ylsulfonyl)-1H-pyrrol-3-yl]methanamine;
(13) 1-[5-(2-fluorophenyl)-1-(pyridin-3-ylsulfonyl)-1H-pyrrol-3-yl]-N-methylmethanamine;
(14) N-methyl-1-[5-(2-methylphenyl)-1-(pyridine-3-ylsulfonyl)-1H-pyrrol-3-yl]methanamine;
(15) 8-[{2,6-dimethylbenzyl}amino]-N-[2-hydroxyethyl]-2,3-dimethylimidazo[1,2-a]pyridine-6-carboxamide;
(16) (7R,8R,9R)-7-(2-methoxyethoxy)-2,3-dimethyl-9-phenyl-7,8,9,10-tetrahydroimidazo[1,2-h][1,7]naphthyridin-8-ol;
(17) 5,6-dimethyl-2-(4-fluoro-phenylamino)-4-(1-methyl-1,2,3,4-tetrahydroisoquinoline-2-yl)pyrimidine;
(18) (S)—N,N,2,3-tetramethyl-8-O-tolyl-3,6,7,8-tetrahydrochromeno[7,8-d]imidazole-5-carboxamide; and
(19) 7-(4-fluorobenzyloxy)-2,3-dimethyl-1-{[(1S,2S)-2-methylcyclopropyl]methyl}-1H-pyrrolo[2,3-d]pyridazine.

3. The method according to claim 1, wherein the compound or salt having the acid pump antagonistic activity is selected from the group consisting of:
(1) (S)-(−)-4-[(5,7-difluoro-3,4-dihydro-2H-chromen-4-yl)oxy]-N,N,2-trimethyl-1H-benzimidazole-6-carboxamide;
(4) (−)-1-(2-methoxyethyl)-N,N,2-trimethyl-8-phenyl-1, 6,7,8-tetrahydrochromeno[7,8-d]imidazole-5-carboxamide;
(13) 1-[5-(2-fluorophenyl)-1-(pyridin-3-ylsulfonyl)-1H-pyrrol-3-yl]-N-methylmethanamine;
(15) 8-[{2,6-dimethylbenzyl} amino]-N-[2-hydroxyethyl]-2,3-dimethylimidazo[1,2-a]pyridine-6-carboxamide; and
(17) 5,6-dimethyl-2-(4-fluoro-phenylamino)-4-(1-methyl-1,2,3,4-tetrahydroisoquinoline-2-yl)pyrimidine.

4. The method according to claim 1, wherein the disease involves a loss of a motor function of a stomach or an intestine of the human or the animal.

5. The method according to claim 1, further comprising administering the compound having the acid pump antagonistic activity or the pharmaceutically acceptable salt thereof in combination with one or two additional active agent(s).

6. The method according to claim 5, wherein the additional active agent is selected from the group consisting of:
piperacillin, lenampicillin, tetracycline, metronidazole, bithmuth citrate and bithmuth subsalicylate.

7. The method according to claim 1, wherein the gastrointestinal motility involves duodenal motility.

* * * * *

UNITED STATES PATENT AND TRADEMARK OFFICE
CERTIFICATE OF CORRECTION

PATENT NO. : 8,648,080 B2
APPLICATION NO. : 13/383056
DATED : February 11, 2014
INVENTOR(S) : Nobuyuki Takahashi et al.

Page 1 of 1

It is certified that error appears in the above-identified patent and that said Letters Patent is hereby corrected as shown below:

In the claims

In column 23, lines 4-6 (claim 2), "(1) (S)-(+4-[(5,7-difluoro-3,4-dihydro-2H-chromen-4-yl)oxy]-N,N,2-trimethyl-1H-benzimidazole-6-carboxamide;", should read
--(1) (S)-(-)-4-[(5,7-difluoro-3,4-dihydro-2H-chromen-4-yl)oxy]-N,N,2-trimethyl-1H-benzimidazole-6-carboxamide;--.

In column 23, lines 7-9 (claim 2), "(2) (S)-(+4-[(5,7-difluoro-3,4-dihydro-2H-chromen-4-yl)oxy]-2-methyl-6-(pyrrolidin-1-ylcarbonyl)-1H-benzimidazole;", should read
--(2) (S)-(-)-4-[(5,7-difluoro-3,4-dihydro-2H-chromen-4-yl)oxy]-2-methyl-6-(pyrrolidin-1-ylcarbonyl)-1H-benzimidazole;--.

In column 23, lines 16-18 (claim 2), "(5) (+8-(4-fluorophenyl)-1-(2-methoxyethyl)-N,N,2-trimethyl-1,6,7,8-tetrahydrochromeno[7,8-d]imidazole-5-carboxamide;", should read
--(5) (-)-8-(4-fluorophenyl)-1-(2-methoxyethyl)-N,N,2-trimethyl-1,6,7,8-tetrahydrochromeno[7,8-d]imidazole-5-carboxamide;--.

In column 24, lines 6-7 (claim 2), "(18) (S)—N,N,2,3-tetramethyl-8-O-tolyl-3,6,7,8-tetrahydrochromeno[7,8-d]imidazole-5-carboxamide; and", should read
--(18) (S)-N,N,2,3-tetramethyl-8-O-tolyl-3,6,7,8-tetrahydrochromeno[7,8-d]imidazole-5-carboxamide; and--.

Signed and Sealed this
Twentieth Day of October, 2015

Michelle K. Lee
*Director of the United States Patent and Trademark Office*